US008669270B2

(12) United States Patent
Higaki et al.

(10) Patent No.: US 8,669,270 B2
(45) Date of Patent: *Mar. 11, 2014

(54) SNS-595 AND METHODS OF USING THE SAME

(75) Inventors: Masaru Higaki, Osaka (JP); Satoshi Nakao, Osaka (JP)

(73) Assignees: Dainippon Sumitomo Pharma Co., Ltd., Osaka (JP); Sunesis Pharmaceuticals, Inc., South San Francisco, CA (US)

( * ) Notice: Subject to any disclaimer, the term of this patent is extended or adjusted under 35 U.S.C. 154(b) by 161 days.

This patent is subject to a terminal disclaimer.

(21) Appl. No.: 13/159,258

(22) Filed: Jun. 13, 2011

(65) Prior Publication Data

US 2011/0312988 A1 Dec. 22, 2011

Related U.S. Application Data

(63) Continuation of application No. 11/080,283, filed on Mar. 14, 2005, now Pat. No. 7,989,468.

(60) Provisional application No. 60/553,578, filed on Mar. 15, 2004.

(51) Int. Cl.
*A61K 31/47* (2006.01)
*A61K 31/4375* (2006.01)
*A61K 47/12* (2006.01)

(52) U.S. Cl.
CPC .............. *A61K 31/4375* (2013.01); *A61K 47/12* (2013.01)
USPC ......................................................... 514/300

(58) Field of Classification Search
CPC ................................................. A61K 31/4375
See application file for complete search history.

(56) References Cited

U.S. PATENT DOCUMENTS

| | | | |
|---|---|---|---|
| 5,078,996 A | 1/1992 | Conlon, III et al. | |
| 5,817,669 A | 10/1998 | Tomita et al. | |
| 7,829,577 B2* | 11/2010 | Higaki et al. | 514/300 |
| 8,138,202 B2* | 3/2012 | Sudhakar et al. | 514/300 |
| 2003/0216316 A1 | 11/2003 | Haran-Ghera et al. | |
| 2008/0063642 A1 | 3/2008 | Adelman et al. | |

FOREIGN PATENT DOCUMENTS

| | | |
|---|---|---|
| JP | 09-221424 | 8/1997 |
| JP | 11-349565 | 12/1999 |
| WO | WO 01/74395 A1 | 10/2001 |
| WO | WO 2005/089756 A1 | 9/2005 |
| WO | WO 2007/028171 A1 | 3/2007 |
| WO | WO 2007/146335 A1 | 12/2007 |
| WO | WO 2008/016678 A1 | 2/2008 |
| WO | WO 2009/054935 A1 | 4/2009 |
| WO | WO 2009/075841 A1 | 6/2009 |

OTHER PUBLICATIONS

Allen, "Complications of Chemotherapy in Patients with Brain and Spinal Cord Tumors," *Ped. Neurosurg.*, vol. 17, No. 4, pp. 218-224, 1991-1992, Database MEDLINE Accession No. 92345081.

Chiba, et al., "Practical Synthesis of AG-7352, Optically Active New Antitumor Agent," Aug. 22-26, 1999, Abstract, 218th ACS National Meeting.

Evanchik, et al., "Non-Clinical Admet, PK, and Biological Activity of SNS-595, a Novel Cell Cycle Inhibitory Antineoplastic Agent," *Drug metabolism reviews*, Aug. 2004, Marcel Dekker,New York, NY, US, vol. 36, No. SUPPL 1, p. 103 XP008073741.

Freireich et al., "Quantitative Comparison of Toxicity of Anticancer Agents in Mouse, Rat, Hamster, Dog, Monkey, and Man," *Cancer Chemotherapy Reports*, 1996, vol. 50, No. 4, pp. 219-244.

Glaspy, et al., "A Dose-Finding and Safety Study of Novel Erythropoiesis Stimulating Protein (NESP) for the Treatment of Anaemia in Patients Receiving Multicycle Chemotherapy," *Br. J. Cancer*, Apr. 2001, vol. 84 (suppl. 1), pp. 17-23, Database CANCERLIT Accession No. 2002-047630.

Herman, et al., "Nabilone: A Potent Antiemetic Cannabinol with Minimal Euphoria," *Biomedicine*, Dec. 1977, vol. 27, No. 9-10, pp. 331-334, Database MEDLINE Accession No. 78104303.

Kashimoto, et al., "Antitumor Activity of a Novel Quinolone Analog AG-7352 in Human Xenograft Models of Leukemia or Drug-Resistant Tumors and in an Experimental Metastatic Tumor Model," *Proc. Am. Assoc. Can. Res. An. Mtg.*, Mar. 2001, vol. 42, p. 102, Database BIOSIS Accession No. 2001:366681.

Lawrence, et al., "SNS-595, a Novel S-Phase Active Cytotoxic, Demonstrates Pharmacologic Properties Appropriate for the Treatment of Advanced Hematologic Malignancies," *Blood*, Nov. 2005, vol. 106, No. 11, Part 2, p. 2378 XP008073743.

Lawrence, et al., "SNS-595, A Novel S-Phase Active Cytotoxic, Exhibits Potent In Vitro and In Vivo Activities, and Has the Potential for Treating Advanced Hematoloic Malignacies," *Proceedings of the Annual Meeting of the American Association for Cancer Research*, Apr. 2006, New York, NY, vol. 47, p. 1110 XP001199684.

Nakano, et al., "Antitumor Activity of a Novel Quinolone DNA Topoisomerase II Inhibitor AG-7352." *Proceedings of the Annual Meeting of the American Association for Cancer Research*, Mar. 1999, New York, NY, vol. 40, p. 115—Abstract 767 XP008073720.

Rustum et al., "1β-Arabinofuranosylcytosine in Therapy of Leukemia: Preclinical and Clinical Overview," *Pharmac. Ther.*, 1992, vol. 56, pp. 307-321.

(Continued)

*Primary Examiner* — James D Anderson

(74) *Attorney, Agent, or Firm* — Jones Day

(57) ABSTRACT

The present invention relates to SNS-595 and methods of treating cancer using the same.

26 Claims, 1 Drawing Sheet

(56) References Cited

OTHER PUBLICATIONS

Ryffel, "Safety of Human Recombinant Proteins," *Biomed. Environ. Sci.*, Mar. 1997, vol. 10, No. 1, pp. 65-72, Database CANCERLIT Accession No. 97254190.
Sato, et al., "In Vivo Antitumor Activity of a Novel Quinolone Analogue AG-7352 Against a Borad-Spectrum of Cancers and Drug-Resistant Human Cancers." Abstract, *11th NCI-E0ARTC-AACR symposium on new drugs in cancer therapy*, Nov. 7-10, 2000.
The Oxford Textbook of Oncology, 1995, vol. 1, Oxford University Press, pp. 445-452.
Therasse, et al., "New Guidelines to Evaluate the Response to Treatment in Solid Tumors", *Journal of the National Cancer Institute*, Feb. 2, 2000, vol. 92, No. 3.
Tolcher, et al., "Phase I and Pharmacokinetic Study of NSC 655649, a Rebeccamycin Analog with Topoisomerase Inhibitory Properties," *Journal of Clinical Oncology*, Jun. 1, 2001, vol. 19, No. 11.
Tomitra, "Synthesis and Structure-Activity Relationships of Novel 7-Substituted 1.4-Dihydro-4-oxo-1-(2 thiazolyl)-1, 8-naphthyridine-3-carboxylic Acids as Antitumor Agents," *J. Med. Chem.*, 2002, vol. 45, pp. 5564-5575.
Tomtia, et al., "Synthesis and Antitumor activity of Novel 7-Substituted 1, 4-dihydro-4-oxo-1-2(2-thiazolyl)-1, 8-naphthyridine-3-carobxylic Acids," BK Abstracts, 217th ACS Nat Mtg., Mar. 21-25, 1999, Database CAPLUS Accession No. 1999:92763.
Tsuzuki, et al., "Efficient stereospecific synthesis of (S,S)-3-methoxy-4-methylaminopyrrolidine," *Tetrahedron: Asymmetry*, 2001, vol. 12, pp. 1793-1799.
Tsuzuki, et al., "Practical Synthesis of (3S,4S)-3-Methoxy-4-Methylaminopyrrolidine," *Tetrahedron: Asymmetry*, 2001, vol. 12, pp. 2989-2997.
Tsuzuki, et al., "Process Research of a Novel Quinolone Antitumor Agent, AG-7352," English Abstract, *The Japanese Society for Process Chemstry*, 2004, Summer Symposium.
Tsuzuki, et al., "Synthesis and Structure-Activity Relationships of Novel 7-Substituted 1,4-Dihydro-4-oxo-1-(2-thiazolyl)-1,8-naphthyridine-3-carboxylic Acids as Antitumor Agents," *J. Med. Chem.*, 2004, vol. 47, pp. 2097-2109.
Tsuzuki, et al., "Synthesis and Structure—Activity Relationships of 3-Substituted 1, 4-Dihydro-4-Oxo-1-(2-Thiazolyl)-1, 8-Naphthridines as Novel Antitumor Agents," *Bioorganic & Medicinal Chemistry Letters*, 2004, vol. 14, pp. 3189-3193.
Tsuzuki, et al., "Synthesis of Optically Active Amine at C-7 Position of New Antitumor Agent AG-7352," Abstract, Molecular Chirality Conference, 1999.
Wright, et al., "SNS-595 Has Synergistic Activity in Vitro with DNA Damaging Agents and Antimetabolites," *Proceedings of the Annual Meeting of the American Association for Cancer Research*, Apr. 2006, New York, NY, vol. 47, p. 504 XP001199686.

* cited by examiner

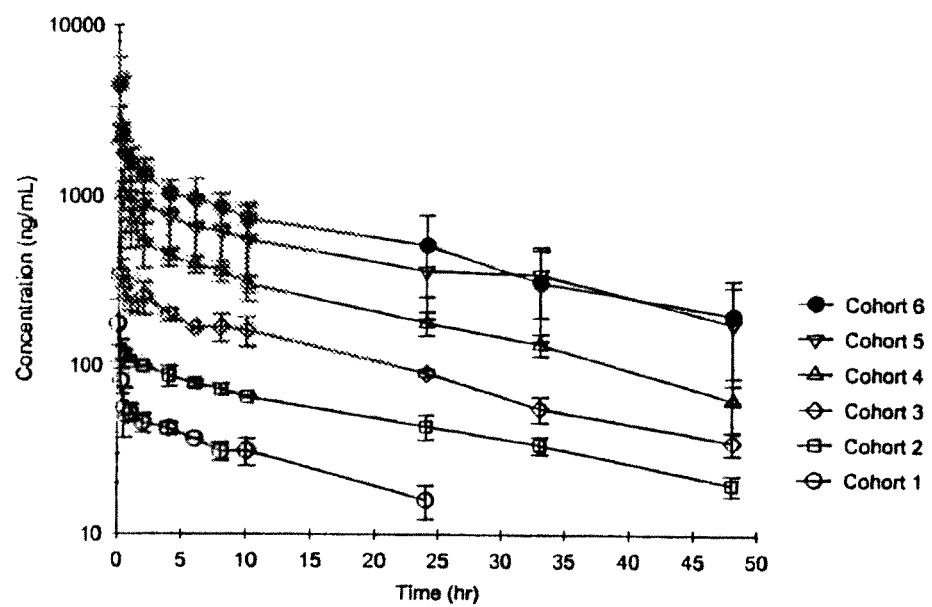

SNS-595 AND METHODS OF USING THE SAME

This application is a continuation of U.S. application Ser. No. 11/080,283 filed Mar. 14, 2005, which claims priority to U.S. Application No. 60/553,578 filed Mar. 15, 2004, each of which are incorporated herein by reference.

PARTIES TO A JOINT RESEARCH AGREEMENT

The subject matter of this application arises in part from a joint research agreement between Sunesis Pharmaceuticals, Inc. and Dainippon Sumitomo Pharma Co., Ltd.

SNS-595 is novel naphthyridine cytotoxic agent that was previously known as AG-7352 (see e.g., Tsuzuki et al., *Tetrahedron-Asymmetry* 12: 1793-1799 (2001) and U.S. Pat. No. 5,817,669). The chemical name of SNS-595 is (+)-1,4-dihydro-7-[3S,4S]-3-methoxy-4-(methylamino)-1-pyrrolidinyl]-4-oxo-1-(2-thiazoyl)-1,8-naphthyridine-3-carboxylic acid and has the structure shown below

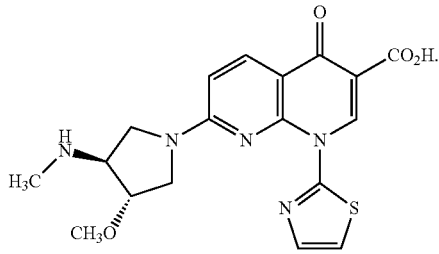

The present invention relates to pharmaceutical compositions and methods of using SNS-595 to treat cancer.

DESCRIPTION OF THE FIGURES

FIG. 1 depicts the plasma concentrations of SNS-595 over time among the various patient cohorts.

DETAILED DESCRIPTION

In one aspect of the present invention, pharmaceutical composition is provided comprising:
a) SNS-595 and
b) an acid
in an aqueous solution wherein the pH of the solution is 2-3.5. As used herein, a numerical range is intended to be inclusive. For example, the range of pH 2-3.5 includes both pH 2 and pH 3.5. In one embodiment, the pH of the composition is 2-3. In another embodiment, the pH of the composition is 2.3-2.7. As used herein, an aqueous solution is a liquid comprising water.

Suitable examples of acids include both organic and inorganic acids such as acetic acid, ascorbic acid, benzene-sulfonic acid, ethanesulfonic acid, glycolic acid, hydrogen chloride, hydrogen bromide, hydroxyethanesulfonic acid, lactic acid, maleic acid, methanesulfonic acid, proprionic acid, succinic acid, sulfuric acid, trifluoroacetic acid, and toluenesulfonic acid. In one embodiment, the acid is hydrochloric acid, methanesulfonic acid or lactic acid. In another embodiment, the acid is methanesulfonic acid.

In another embodiment, the pharmaceutical composition further comprises a tonicity agent. Suitable examples of a tonicity agent include amino acids (e.g., alanine and glycine), electrolytes (e.g., sodium chloride and potassium chloride), monosaccharides (e.g. glucose or galactose), disaccharides (e.g. sucrose) and hexahydric alcohols (e.g., mannitol and sorbitol). In another embodiment, the tonicity agent is sodium chloride, glucose, mannitol, or sorbitol. In another embodiment, the tonicity agent is a hexahydric alcohol. In another embodiment, the tonicity agent is sorbitol.

SNS-595 is a cytotoxic agent for the treatment of cancer. The types of cancers that can be treated using the inventive methods include but are not limited to: bladder cancer, breast cancer, cervical cancer, colon cancer (including colorectal cancer), esophageal cancer, head and neck cancer, leukemia, liver cancer, lung cancer (both small cell and non-small cell), lymphoma, melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer.

In another aspect of the invention, a method of using SNS-595 to treat a human cancer is provided. The method comprises administering to a patient on the basis of body surface area, a dose of 10 mg/m$^2$-150 mg/m$^2$ of SNS-595. Body surface area calculations can be calculated for example, with the Mosteller formula wherein:

BSA (m$^2$)=square root of [(height (cm)×weight (kg)/3600].

In another embodiment, the dose is 10 mg/m$^2$-100 mg/m$^2$. In another embodiment, the dose is 30 mg/m$^2$-75 mg/m$^2$. In another embodiment, the dose is 40 mg/m$^2$-80 mg/m$^2$. In another embodiment, the dose is 50 mg/m$^2$-90 mg/m$^2$.

In another embodiment the dose is 20 mg/m$^2$-30 mg/m$^2$. In another embodiment the dose is 25 mg/m$^2$-35 mg/m$^2$. In another embodiment the dose is 40 mg/m$^2$-50 mg/m$^2$. In another embodiment the dose is 45 mg/m$^2$-55 mg/m$^2$. In another embodiment the dose is 50 mg/m$^2$-60 mg/m$^2$. In another embodiment the dose is 55 mg/m$^2$-65 mg/m$^2$. In another embodiment the dose is 60 mg/m$^2$-70 mg/m$^2$. In another embodiment the dose is 65 mg/m$^2$-75 mg/m$^2$. In another embodiment the dose is 70 mg/m$^2$-80 mg/m$^2$. In another embodiment the dose is 75 mg/m$^2$-85 mg/m$^2$. In another embodiment the dose is 80 mg/m$^2$-90 mg/m$^2$. In another embodiment the dose is 85 mg/m$^2$-95 mg/m$^2$. In another embodiment the dose is 90 mg/m$^2$-100 mg/m$^2$.

In another embodiment the dose is 95 mg/m$^2$-105 mg/m$^2$. In another embodiment the dose is 100 mg/m$^2$-110 mg/m$^2$. In another embodiment the dose is 105 mg/m$^2$-115 mg/m$^2$. In another embodiment the dose is 110 mg/m$^2$-120 mg/m$^2$. In another embodiment the dose is 115 mg/m$^2$-125 mg/m$^2$. In another embodiment the dose is 120 mg/m$^2$-130 mg/m$^2$. In another embodiment the dose is 125 mg/m$^2$-135 mg/m$^2$. In another embodiment the dose is 130 mg/m$^2$-140 mg/m$^2$. In another embodiment the dose is 135 mg/m$^2$-145 mg/m$^2$. In another embodiment the dose is 140 mg/m$^2$-150 mg/m$^2$.

The administered dose of SNS-595 can be delivered simultaneously (e.g. a single bolus injection) or over a 24-hour period (e.g., continuous infusion over time or divided bolus doses over time) and is repeated until the patient experiences stable disease or regression, or until the patient experiences disease progression or unacceptable toxicity. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The administered dose of SNS-595 can be expressed in units other than as mg/m$^2$. For example, doses can be expressed as mg/kg. One of ordinary skill in the art would readily know how to convert doses from mg/m$^2$ to mg/kg to given either the height or weight of a subject or both (see e.g., http:///www.fda.gov/cder/cancer/animalframe.htm). For example, a dose of 10 mg/m$^2$-150 mg/m$^2$ for a 65 kg human is approximately equal to 0.26 mg/kg-3.95 mg/kg.

In another aspect of the present invention, SNS-595 is administered according to a dosing schedule. In one embodiment, the method comprises:
  i) administering a dose of 10 mg/m$^2$-150 mg/m$^2$ of SNS-595 to a patient;
  ii) waiting a period of at least one day where the subject is not administered any SNS-595;
  iii) administering another dose of 10 mg/m$^2$-150 mg/m$^2$ of SNS-595 to the patient; and,
  iv) repeating steps ii)-iii) a plurality of times.

For example, if the waiting period were 6 days, then the initial dose of SNS-595 is administered on Day 1 (step i); the waiting period is six days (step ii); and the following dose of SNS-595 is administered on Day 8 (step iii). Other exemplary time periods include 2 days, 3 days, 13 days, 20 days, and 27 days. In another embodiment, the waiting period is at least 2 days and steps ii) through iii) are repeated at least three times. In another embodiment, the waiting period is at least 3 days and steps ii) through iii) are repeated at least five times. In another embodiment, the waiting period is at least 3 days and steps ii) through iii) are repeated at least three times. In another embodiment, the waiting period is at least 3 days and steps ii) through are repeated at least five times. In another embodiment, the waiting period is at least 6 days and steps ii) through iii) are repeated at least three times. In another embodiment, the waiting period is at least 6 days and steps ii) through iii) are repeated at least five times. In another embodiment, the waiting period is at least 20 days and steps ii) through iii) are repeated at least three times. In another embodiment, the waiting period is at least 20 days and steps ii) through iii) are repeated at least five times. In another embodiment, the waiting period is at least 27 days and steps ii) through iii) are repeated at least three times. In another embodiment, the waiting period is at least 27 days and steps ii) through iii) are repeated at least five times.

In another embodiment, the dosing method comprises administering a weekly dose of SNS-595 to a subject. In another embodiment, the dosing method comprises administering a dose of SNS-595 to a subject every two weeks. In another embodiment, the dosing method comprises administering a dose of SNS-595 to a subject every three weeks. In another embodiment, the dosing method comprises administering a dose of SNS-595 to a subject every four weeks.

In another embodiment, the dosing method comprises a cycle wherein the cycle comprises administering a dose of SNS-595 to a subject every week for three weeks followed by a period of at least two weeks where no SNS-595 is administered to said subject and wherein the cycle is repeated a plurality of times. In another embodiment, the period where no SNS-595 is administered is two weeks. In another embodiment, the period where no SNS-595 is administered is three weeks.

In another aspect of the invention, a method of treating a solid tumor is provided. The method comprises:
  i) administering a dose of 10 mg/m$^2$-100 mg/m$^2$ of SNS-595 to a patient;
  ii) waiting a period of at least six days where the subject is not administered any SNS-595;
  iii) administering another dose of 10 mg/m$^2$-100 mg/m$^2$ of SNS-595 to the patient; and,
  iv) repeating steps ii)-iii) a plurality of times.

In another aspect of the invention, a method of treating a hematologic cancer such as leukemias and lymphomas is provided. The method comprises:
  i) administering a dose of 60 mg/m$^2$-150 mg/m$^2$ of SNS-595 to a patient;
  ii) waiting a period of at least two days where the subject is not administered any SNS-595;
  iii) administering another dose of 60 mg/m$^2$-150 mg/m$^2$ of SNS-595 to the patient; and,
  iv) repeating steps ii)-iii) a plurality of times.

In another aspect of the present invention, a method is provided supportive care to patients being treated with SNS-595. The method comprises:
  a) administering to a patient a dose of 10 mg/m$^2$-150 mg/m$^2$ of SNS-595 and
  b) administering a therapeutically effective amount of a supportive care agent.

The supportive care agent is any substance that prevents or manages an adverse effect from SNS-595 treatment and is administered according to the appropriate dosing regimen for that substance. For example, different supportive care agents for treating nausea have different dosing regimen. While some are administered prophylactically, others are co-administered with SNS-595 while still others are administered after the administration of SNS-595. Illustrative examples of supportive care agents their doses and dosing regimens are found in The Physician's Desk Reference.

In one embodiment, the supportive care agent is an antiemetic. Illustrative examples of antiemetics include but are not limited to phenothiazines, butyrophenones, benzodiazapines, corticosteroids, serotonin antagonists, cannabinoids, and NK$_1$ receptor antagonists. Examples of phenothiazine antiemetics include prochlorperazine and trimethobenzamide. An example of a butyrophenone antiemetic is haloperidol. An example of a benzodiazapine antiemetic is lorazepam. An example of a corticosteroid antiemetic is dexamethasone. Examples of a serotonin antagonist antiemetic include ondansetron, granisetron, and dolasetron. An example of a cannabinoid antiemetic is dronabinol. An example of an MCI receptor antagonist is aprepitant.

In another embodiment, the antiemetic is prochlorperazine. In another embodiment, the antiemetic is prochlorperazine and the therapeutically effective amount is 10 mg. In another embodiment, the antiemetic is prochlorperazine and the therapeutically effective amount is an oral dose of 10 mg before the administration of SNS-595. In another embodiment, the antiemetic is prochlorperazine and the therapeutically effective amount is an oral dose of 10 mg every four to six hours as needed after the administration of SNS-595.

In another embodiment, the antiemetic is dexamethasone. In another embodiment, the antiemetic is dexamethasone and the therapeutically effective amount is at least 4 mg. In another embodiment, the antiemetic is dexamethasone and the therapeutically effective amount is an oral dose of 4 mg before the administration of SNS-595. In another embodiment, the antiemetic is dexamethasone and the therapeutically effective amount is an oral dose of 8 mg before the administration of SNS-595. In another embodiment, the antiemetic is dexamethasone and the therapeutically effective amount is an intravenous dose of between about 10 mg and about 20 mg before the administration of SNS-595. In another embodiment, the antiemetic is dexamethasone and the therapeutically effective amount is an oral dose of 4 mg every six to twelve hours as needed after the administration of SNS-595.

In another embodiment, the antiemetic is lorazepam. In another embodiment, the antiemetic is lorazepam and the therapeutically effective amount is 1 mg. In another embodiment, the antiemetic is lorazepam and the therapeutically effective amount is an oral dose of 1 mg before the administration of SNS-595. In another embodiment, the antiemetic is lorazepam and the therapeutically effective amount is an intravenous dose of 1 mg before the administration of SNS-595. In another embodiment, the antiemetic is lorazepam and the therapeutically effective amount is an oral dose of 1 mg every four to six hours as needed after the administration of SNS-595.

In another embodiment, the antiemetic is dolasetron. In another embodiment, the antiemetic is dolasetron and the therapeutically effective amount is 100 mg. In another embodiment, the antiemetic is dolasetron and the therapeutically effective amount is an oral dose of 100 mg before the administration of SNS-595. In another embodiment, the antiemetic is dolasetron and the therapeutically effective amount is an intravenous dose of 100 mg before the administration of SNS-595.

In another embodiment, the antiemetic is ondansetron. In another embodiment, the antiemetic is ondansetron and the therapeutically effective amount is at least 10 mg. In another embodiment, the antiemetic is ondansetron and the therapeutically effective amount is an intravenous dose of 10 mg before the administration of SNS-595. In another embodiment, the antiemetic is ondansetron and the therapeutically effective amount is an intravenous dose of 32 mg before the administration of SNS-595.

In another embodiment, the antiemetic is granisetron. In another embodiment, the antiemetic is granisetron and the therapeutically effective amount is 10 µg/kg. In another embodiment, the antiemetic is granisetron and the therapeutically effective amount is an intravenous dose of 10 µg/kg before the administration of SNS-595. In another embodiment, the antiemetic is granisetron and the therapeutically effective amount is at least 1 mg. In another embodiment, the antiemetic is granisetron and the therapeutically effective amount is an oral dose of 1 mg before the administration of SNS-595. In another embodiment, the antiemetic is granisetron and the therapeutically effective amount is an oral dose of 2 mg before the administration of SNS-595.

In another embodiment, the antiemetic is aprepitant. In another embodiment, the antiemetic is aprepitant and the therapeutically effective amount is at least 80 mg. In another embodiment, the antiemetic is aprepitant and the therapeutically effective amount is an oral dose of 125 mg before the administration of SNS-595. In another embodiment, the antiemetic is aprepitant and the therapeutically effective amount is a daily oral dose of 80 mg for at least two days after the administration of SNS-595.

In another embodiment, the supportive care agent is a hematopoietic agent. A hematopoietic agent is a molecule that stimulates hematopoiesis. Illustrative examples of hematopoietic agents include but are not limited to granulocyte colony stimulating factor (G-CSF), CSF), granulocyte macrophage colony stimulating factor (GM-CSF), erythropoietin and erythropoiesis stimulating protein, and derivatives thereof. Examples of G-CSF include but are not limited to filgrastim and its derivatives including pegfilgrastim. An example of GM-CSF includes sargramostim. An example of erythropoietin is epoetin alfa. An example of erythropoiesis stimulating protein is darbepoetin alfa.

In another embodiment, the hematopoietic agent is G-CSF. In another embodiment, the hematopoietic agent is filgrastim. In another embodiment, the hematopoietic agent is filgrastim and the therapeutically effective amount is at least 4 µg/kg. In another embodiment, the hematopoietic agent is filgrastim and the therapeutically effective amount is a daily dose of at least 4 µg/kg for at least 7 days after the administration of SNS-595. In another embodiment, the hematopoietic agent is filgrastim and the therapeutically effective amount is a daily subcutaneous dose of between about 4 µg/kg and about 8 µg/kg for at least 7 days starting from the third day after the administration of SNS-595. In another embodiment, the hematopoietic agent is filgrastim and the therapeutically effective amount is a daily subcutaneous dose of between about 4 µg/kg and about 10 µg/kg for at least 14 days starting from the third day after the administration of SNS-595.

In another embodiment, the hematopoietic agent is pegfilgrastim. In another embodiment, the hematopoietic agent is pegfilgrastim and the therapeutically effective amount is 6 mg. In another embodiment, the hematopoietic agent is pegfilgrastim and the therapeutically effective amount is a daily subcutaneous dose of 6 mg after the administration of SNS-595. In another embodiment, the hematopoietic agent is pegfilgrastim and the therapeutically effective amount is 100 µg/kg. In another embodiment, the hematopoietic agent is pegfilgrastim and the therapeutically effective amount is a daily dose of 100 µg/kg after the administration of SNS-595.

In another embodiment, the hematopoietic agent is GM-CSF. In another embodiment, the hematopoietic agent is sargramostim. In another embodiment, the hematopoietic agent is sargramostim and the therapeutically effective amount is 250 µg/m². In another embodiment, the hematopoietic agent is sargramostim and the therapeutically effective amount is a daily intravenous or subcutaneous dose of 250 µg/m². In another embodiment, the hematopoietic agent is sargramostim and the therapeutically effective amount is a daily intravenous or subcutaneous dose of 250 µg/m² as needed starting from the third day after the administration of SNS-595. In another embodiment, the hematopoietic agent is sargramostim and the therapeutically effective amount is a daily intravenous or subcutaneous dose of 250 µg/m² as needed starting from the tenth day after the administration of SNS-595.

In another embodiment, the hematopoietic agent is erythropoietin. In another embodiment, the hematopoietic agent is epoetin alfa. In another embodiment, the hematopoietic agent is epoetin alfa and the therapeutically effective amount is at least 150 units/kg. In another embodiment, the hematopoietic agent is epoetin alfa and the therapeutically effective amount is an intravenous or subcutaneous dose of 150 units/kg three times a week after the administration of SNS-595. In another embodiment, the hematopoietic agent is epoetin alfa and the therapeutically effective amount is an intravenous or subcutaneous dose of 300 units/kg three times a week after the administration of SNS-595. In another embodiment, the hematopoietic agent is epoetin alfa and the therapeutically effective amount is 40,000 units. In another embodiment, the hematopoietic agent is epoetin alfa and the therapeutically effective amount is a weekly dose of 40,000 units after the administration of SNS-595.

In another embodiment, the hematopoietic agent is erythropoiesis stimulating protein. In another embodiment, the hematopoietic agent is darbepoetin alfa. In another embodiment, the hematopoietic agent is darbepoetin alfa and the therapeutically effective amount is between about 1.5 µg/kg and about 4.5 µg/kg. In another embodiment, the hematopoietic agent is darbepoetin alfa and the therapeutically effective amount is a weekly dose of between about 1.5 µg/kg and about 4.5 µg/kg.

All cited references are incorporated herein by reference.

EXAMPLE 1

Pharmaceutical Composition Suitable for Injection or Intravenous Infusion

Acidic compositions (<pH 4) provided the appropriate balance of increased solubility of SNS-595 and desirable pharmaceutical properties (e.g. increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

EXAMPLE 2

Pharmacokinetics of SNS-595 in Cancer Patients

SNS-595 was administered to enrolled patients for up to six cycles. A cycle is defined as a three-week period, with SNS-595 administered on the first day of each cycle (day 0), followed by at least 21 days of observation. SNS-595 was administered to cohorts of at least 3 patients and dose escalation occurred by sequential cohort. Doses of SNS-595 were linear with AUC∞ and its pharmacokinetic properties were remarkably consistent among patients in the same cohort. FIG. 1 depicts the plasma concentrations of SNS-595 over time among the various patient cohorts and Table 1 shows the pharmacokinetic parameters derived there from.

TABLE 1

| Dose (mg/m2) | HL (hr) | C0 (ng/mL) | Cmax (ng/mL) | AUClast (hr * ng/mL) | AUCINF_obs (hr * ng/mL) | CL_obs (mL/min/kg) | Vs_obs (L/kg) | Vss_obs (L/kg) | MRTINF_obs (hr) |
|---|---|---|---|---|---|---|---|---|---|
| 3 | 18.27 | 152.28 | 138.00 | 750.00 | 1138.68 | 1.14 | 1.58 | 1.44 | 21.96 |
| SD | 4.871 | 82.282 | 50.568 | 87.822 | 263 | 0.318 | 0.297 | 0.277 | 6.836 |
| 6 | 20.00 | 370.00 | 347.00 | 2400.00 | 2990.29 | 0.71 | 1.28 | 1.24 | 29.05 |
| SD | 0.327 | 243.590 | 214.98 | 170.556 | 245.64 | 0.153 | 0.295 | 0.218 | 1.15 |
| 12 | 17.81 | 2888.00 | 2200.07 | 5386.53 | 6329.18 | 0.78 | 1.17 | 1.07 | 23.07 |
| SD | 3.898 | 1302.71 | 1055.146 | 292.281 | 181.804 | 0.128 | 0.258 | 0.184 | 5.021 |
| 24 | 16.14 | 2924.46 | 2703.33 | 11133.03 | 12653.32 | 0.83 | 1.15 | 1.08 | 21.65 |
| SD | 2.801 | 2884.702 | 2573.02 | 488.453 | 851.458 | 0.108 | 0.124 | 0.155 | 5.261 |
| 48 | 21.32 | 1964.52 | 2888.00 | 21093.53 | 27347.38 | 0.98 | 1.57 | 1.40 | 28.90 |
| SD | 8.32 | 189.677 | 2379.895 | 9405.348 | 14382.787 | 0.616 | 0.587 | 0.47 | 8.91 |
| 60 | 17.63 | 4797.47 | 4537.50 | 28112.17 | 33416.18 | 0.83 | 1.20 | 1.08 | 23.71 |
| SD | 4.15 | 2215.20 | 1947.89 | 9127.12 | 13081.44 | 0.352 | 0.37 | 0.218 | 8.93 |

What is claimed is:

1. A pharmaceutical composition comprising (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and an acid, wherein the pH of the composition is 2-3.5 when measured in an aqueous solution in which the (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is present in an amount of 10 mg per mL.

2. The pharmaceutical composition of claim 1, wherein the acid is selected from acetic acid, ascorbic acid, benzenesulfonic acid, ethanesulfonic acid, glycolic acid, hydrogen bromide, hydroxyethanesulfonic acid, lactic acid, maleic acid, propionic acid, succinic acid, sulfuric acid, trifluoroacetic acid and toluenesulfonic acid.

3. The pharmaceutical composition of claim 1, wherein the pH of the composition is 2.3-2.7 when measured in aqueous solution.

4. The pharmaceutical composition of claim 1 further comprising a tonicity agent.

5. The pharmaceutical composition of claim 4, wherein the tonicity agent is selected from the group consisting of amino acids, electrolytes, monosaccharides, disaccharides, and hexahydric alcohols.

6. The pharmaceutical composition of claim 5, wherein the tonicity agent comprises sorbitol.

7. The pharmaceutical composition of claim 1, wherein the pH of the composition is 2-3 when measured in aqueous solution.

8. The pharmaceutical composition of claim 1, wherein the pH of the composition is about 2.5 when measured in aqueous solution.

9. The pharmaceutical composition of claim 1 that is formulated for intravenous administration.

10. The pharmaceutical composition of claim 1 further comprising water.

11. The pharmaceutical composition of claim 10, wherein (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is present in an amount of 10 mg/mL.

12. The pharmaceutical composition of claim 10 further comprising sorbitol in an amount of 45 mg per ml.

13. The pharmaceutical composition of claim 10, wherein the composition comprises about 100 mg of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and about 450 mg of sorbitol per 10 mL of the composition.

14. The pharmaceutical composition of claim 13, wherein the pH of the composition is about 2.5 when measured in aqueous solution.

15. A powder consisting essentially of the composition of claim 1.

16. A lyophilized powder consisting essentially of the composition of claim 1.

17. A lyophilized powder consisting essentially of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and an acid, wherein the lyophilized powder is suitable for reconstitution in sterile water to obtain a composition at pH 2-3.5 in which the (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is present in an amount of 10 mg per mL.

18. An aqueous pharmaceutical composition comprising about 10 mg/mL of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, about 45 mg/mL of sorbitol, and an acid, wherein the pH of the composition is about 2.3 to about 2.7.

19. The aqueous pharmaceutical composition of claim 18, wherein the pH of the composition is about 2-3.5.

20. The aqueous pharmaceutical composition of claim 19, wherein the pH of the composition is about 2.3-2.7.

21. The aqueous pharmaceutical composition of claim 20, wherein the pH of the composition is about 2.5.

22. A product formed by a process of contacting about 100 mg of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, about 450 mg of sorbitol and an acid in 10 mL aqueous solvent, wherein the pH of the product is about 2.3 to about 2.7.

23. A method of treating cancer comprising administering the composition of claim 1 to a patient in need of treatment of cancer.

24. A method of treating cancer comprising administering the composition of claim 14 to a patient in need of treatment of cancer.

25. A method of treating cancer comprising administering the composition of claim 18 to a patient in need of treatment of cancer.

26. The pharmaceutical composition of claim 1, wherein the acid is an organic acid.

* * * * *